US012594392B2

(12) United States Patent
Alqarni

(10) Patent No.: US 12,594,392 B2
(45) Date of Patent: Apr. 7, 2026

(54) MOVABLE TIP BOUGIE DEVICE

(71) Applicant: Imam Abdulrahman Bin Faisal University, Dammam (SA)

(72) Inventor: Abdulrahman Alqarni, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 742 days.

(21) Appl. No.: 17/994,768

(22) Filed: Nov. 28, 2022

(65) Prior Publication Data

US 2024/0173501 A1 May 30, 2024

(51) Int. Cl.
*A61M 16/04* (2006.01)

(52) U.S. Cl.
CPC .... *A61M 16/0488* (2013.01); *A61M 16/0418* (2014.02); *A61M 2205/583* (2013.01)

(58) Field of Classification Search
CPC .......... A61M 16/0418; A61M 16/0429; A61M 16/0488; A61M 16/0497; A61M 2205/583; A61M 25/0102; A61B 1/267
See application file for complete search history.

(56) References Cited

U.S. PATENT DOCUMENTS

| | | | | |
|---|---|---|---|---|
| 4,353,358 A | * | 10/1982 | Emerson | A61B 1/31 |
| | | | | 600/146 |
| 6,718,970 B2 | * | 4/2004 | Sniadach | A61M 16/0409 |
| | | | | 128/207.14 |
| 6,761,171 B2 | | 7/2004 | Toti et al. | |
| 9,199,051 B2 | | 12/2015 | Booth | |
| 10,080,854 B1 | * | 9/2018 | Pifer | A61M 16/0488 |
| 10,953,177 B2 | | 3/2021 | Karlsson et al. | |
| 10,974,005 B1 | * | 4/2021 | Sun | A61M 16/0418 |
| 2002/0096177 A1 | * | 7/2002 | Toti | A61M 16/0418 |
| | | | | 128/200.26 |
| 2014/0114132 A1 | | 4/2014 | De Domenico | |
| 2014/0123976 A1 | * | 5/2014 | Mccormick | A61M 16/0488 |
| | | | | 128/200.26 |
| 2018/0250484 A1 | * | 9/2018 | McCormick | A61B 1/05 |
| 2020/0023151 A1 | * | 1/2020 | Karlsson | A61B 1/0051 |
| 2020/0338291 A1 | | 10/2020 | Ananthanarayanan et al. | |

OTHER PUBLICATIONS

FlexTip Bougie—Tracheal Tube—IS Innoventa ; 4 Pages.

* cited by examiner

*Primary Examiner* — Joseph D. Boecker
(74) *Attorney, Agent, or Firm* — Oblon, McClelland, Maier & Neustadt, L.L.P.

(57) ABSTRACT

A movable bougie tip device includes a tip section having a tip, a holder, and a recoiled wire and a bougie section having a bougie, a silk thread, and a slide button located at a first end thereof. The slide button adjusts an angle of the tip relative to the bougie. The silk thread is disposed within a body of the bougie and extends through an outer surface of the tip from the body of the bougie through an opening and protrudes out the tip. The holder holds the silk thread at a distal end of the tip section. The tip bends at an angle ranging from 30° to 90° relative to the bougie, and the recoiled wire prevents kinking of the tip.

17 Claims, 5 Drawing Sheets

MOVABLE TIP BOUGIE DEVICE

BACKGROUND

Technical Field

The present disclosure is directed to a medical device used for a tracheal intubation procedure, and particularly, to a movable tip bougie device used for guiding a silk thread during a tracheal intubation procedure.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

An endotracheal intubation procedure, otherwise known as an airway maintenance method, is performed for a patient who is suffering from respiratory failure, airway obstruction, or a patient who needs breathing support while the patient is under anaesthesia. During the intubation procedure, an endotracheal tube is intubated into the trachea through the mouth and then through the oral cavity. Accordingly, the endotracheal tube is fabricated in a shape that is more or less identical to a curved structure of the human body through which the endotracheal tube passes during the intubation procedure. Further, the intubation procedure includes an endotracheal tube introducer, which is otherwise known as a bougie, for intubating the endotracheal tube into the trachea.

U.S. Pat. No. 9,199,051B2 describes a device that is used with an endotracheal tube. The device includes a shaft having a tip at a distal end thereof and a cord having first end portion coupled to a wall of the shaft and a handle operationally attached to a second end the cord for pulling the cord distally to move the tip away from a central longitudinal axis of the shaft. The shaft further includes a flexible region having a spring to allow movement of the tip. However, the device lacks features for providing controlled movement of the tip. The presence of a spring makes the design and structure of the device complex.

US20200338291A1 describes a tracheal tube insertion facilitator having an outer cylindrical member bent forwards and an inner hollow stylet that serves the dual purpose of providing strength to the bougie and enabling jet ventilation through its ports. However, the tracheal tube insertion facilitator lacks features to adjust the tip angle.

Accordingly, it is one object of the present disclosure to provide a low cost bougie with a movable tip which gives more control and manipulation during tracheal intubation procedure. It is also an object of the present disclosure to develop an inexpensive bougie and tip of the bougie which can be fabricated with less complexity and can be controlled manually for pediatric and neonatal care.

SUMMARY

In an exemplary embodiment, a movable tip bougie device is described. The movable tip bougie device includes a tip section and a bougie section. The bougie section includes a bougie body, a silk thread, and a slide button located at a first end of the bougie section. The slide button is configured to mechanically adjust an angle of a tip disposed on a distal end of the tip section relative to the bougie body by action of the slide button through the silk thread. A first end of the silk thread is connected to the slide button and a second end of the silk thread is connected to the tip. The tip section includes the tip, a holder, and a recoiled wire. The silk thread extends through an outer surface of the tip from the body of the bougie through an opening. The holder is configured to hold the silk thread at the distal end of the tip section. The recoiled wire is helically coiled around the tip. The tip section is connected to the bougie section through a hinge and is configured to move backwards toward the bougie section on retraction of the slide button and forward on pushing the slide button forward.

In some embodiments, the tip is fabricated of polyvinyl chloride (PVC).

In some embodiments, the slide button has a top surface and a bottom surface and a flat circumferential edge between the top surface and bottom surface, wherein the flat circumferential edge includes a notch to engage with the bougie body.

In some embodiments, the body of the bougie has at least seven grooves in which the slide button slides into an individual groove to adjust the angle of the tip by at least 10°.

In some embodiments, the recoiled wire is fabricated of stainless steel.

In some embodiments, the recoiled wire is spirally wound around an interior of the tip.

In some embodiments, the tip section further includes a clipper to align the silk thread through the tip.

In some embodiments, the silk thread is a fiber.

In some embodiments, a length of a slit is from 5% to 40% of an entire length of the bougie body.

In some embodiments, the tip is configured to bend up to 90°, preferably from 60° to 90° relative to a longitudinal axis of the bougie body when the slide button slides towards the first end of the bougie body.

In some embodiments, the tip is configured to bend from 30° to 50° relative to a longitudinal axis of the bougie body when the slide button slides towards the first end of the bougie section.

In some embodiments, the bougie body is substantially cylindrical and a ratio of the length of the bougie body to an outer width of the bougie body is from 5:1 to 40:1.

In some embodiments, the recoiled wire zig-zags across an interior of the tip, so that the recoiled wire runs from a first end of the interior of the tip to a second end of the interior of the tip.

In some embodiments, the first end of the bougie section is substantially elliptical.

In some embodiments, the silk thread runs through the bougie body so that a longitudinal axis of the silk thread is underneath and parallel to a longitudinal axis of the slide button.

In some embodiments, the tip includes one of a coude tip, a reverse coude tip, or a bullet tip.

In some embodiments, a second groove situated between a first groove and a third groove is equidistant from both the first groove and the third groove.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained

Figure 1:
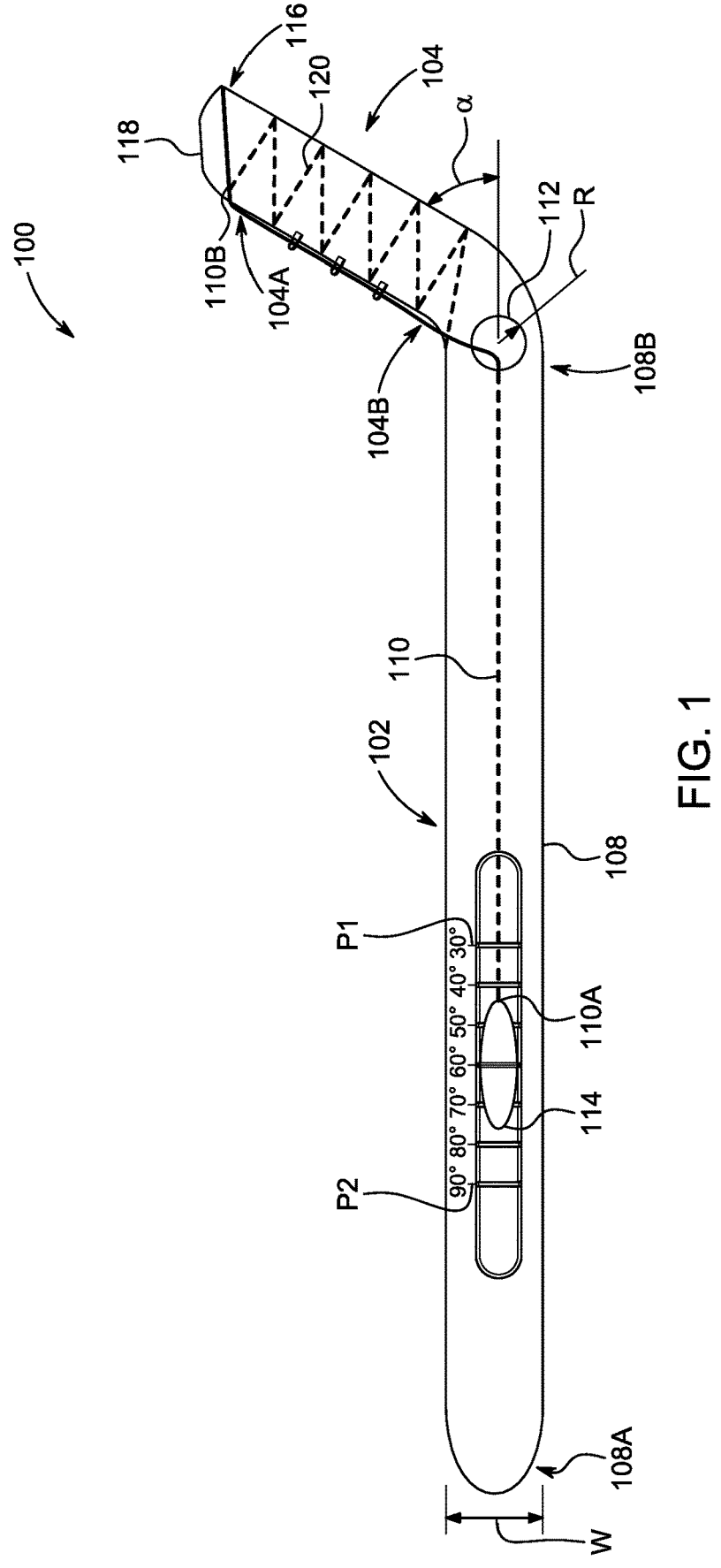
Figure 2:
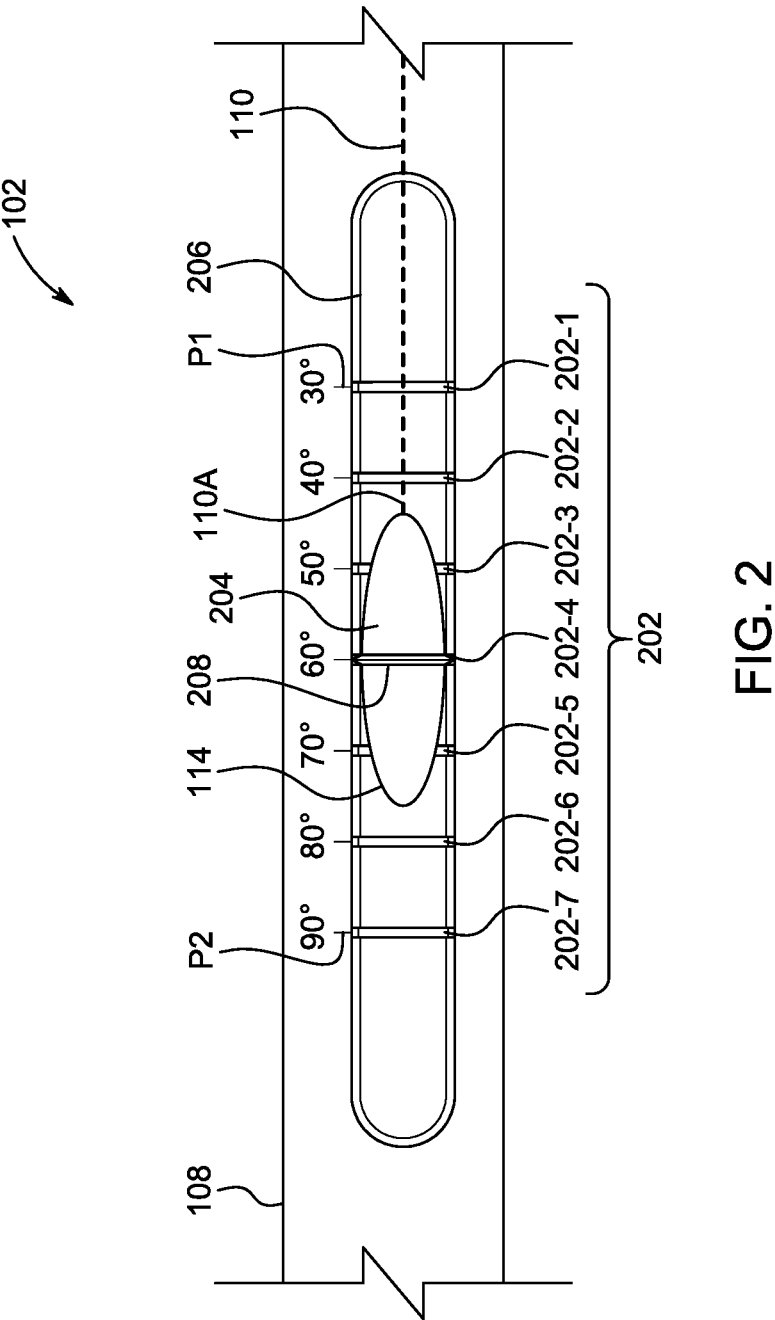
Figure 3:
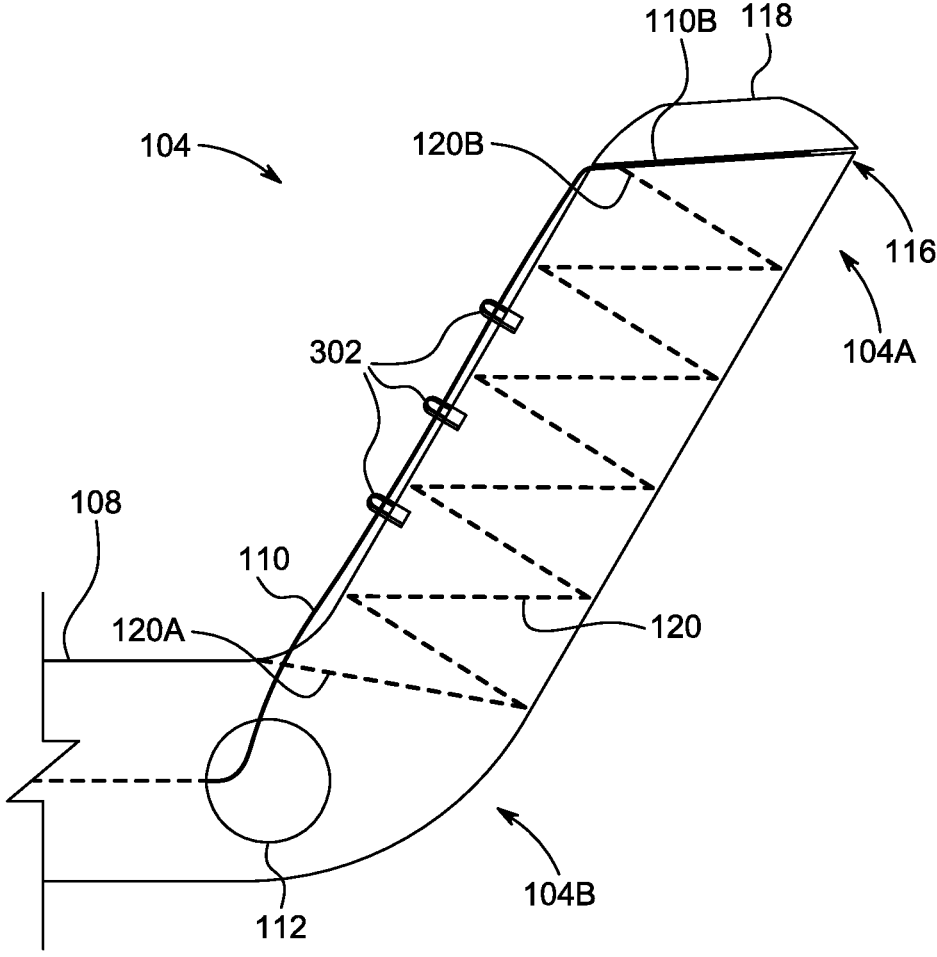
Figure 4A:
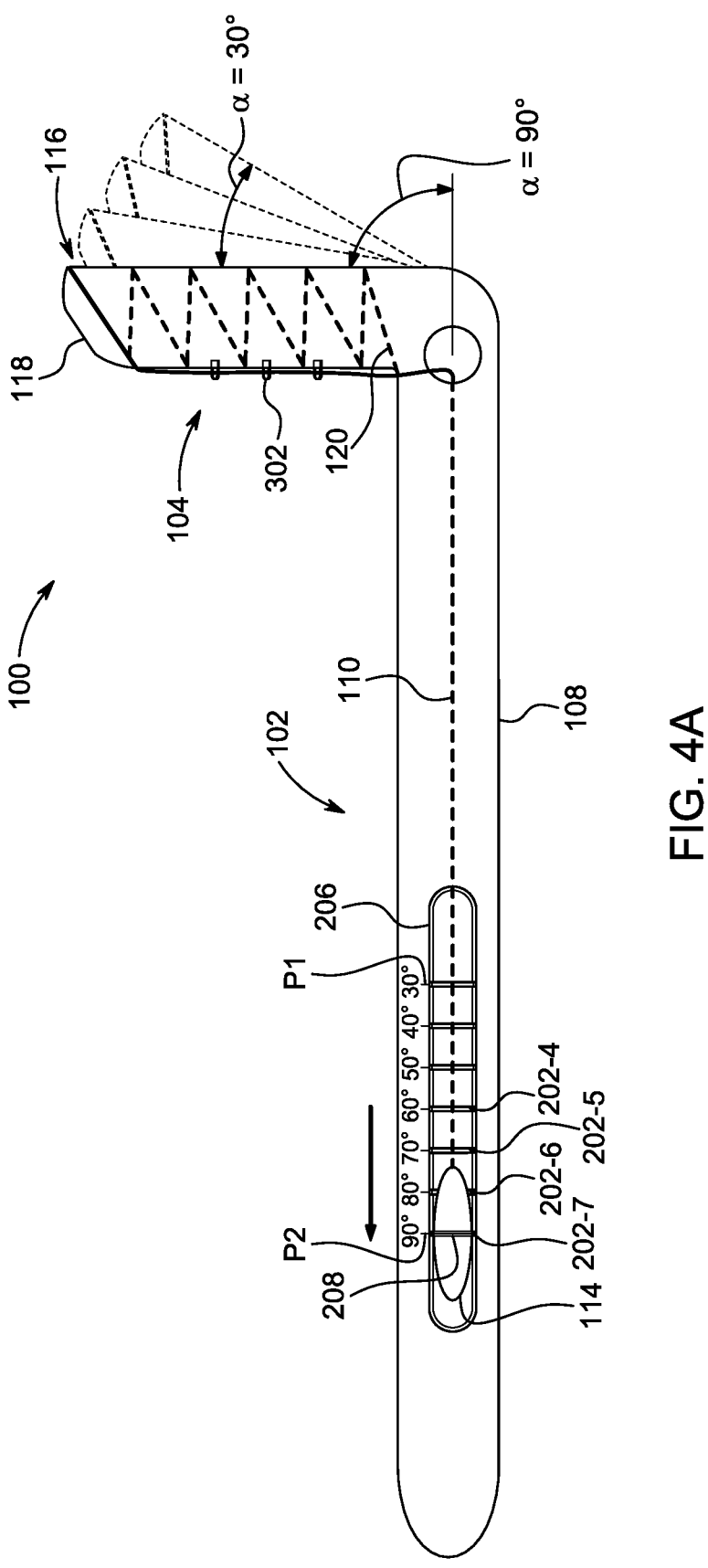
Figure 4B:
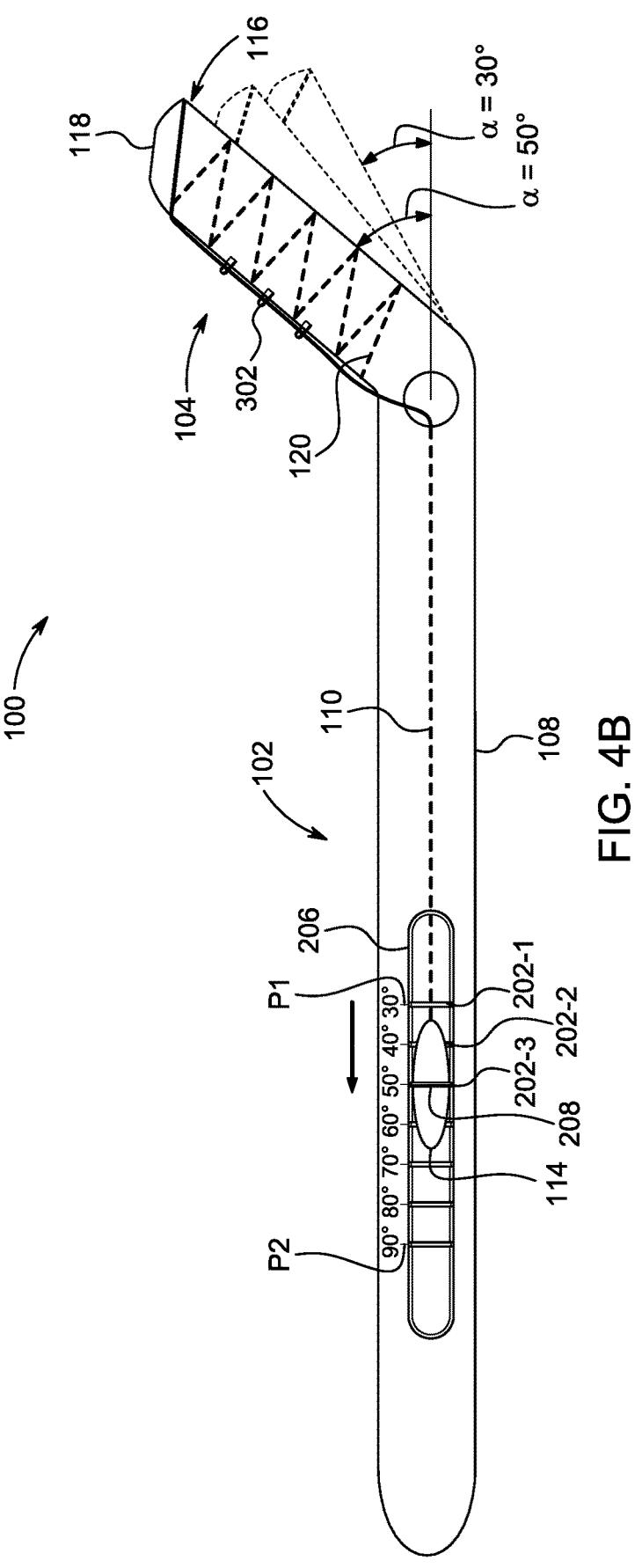

3 as the same becomes better understood by reference to the following detailed description when considered in connection with the accompanying drawings, wherein:

FIG. 1 is a schematic perspective view of a movable tip bougie device, according to certain embodiments;

FIG. 2 is an enlarged view of a portion of the movable tip bougie device of FIG. 1 showing a slide button, according to certain embodiments;

FIG. 3 is an enlarged view of a portion of the movable tip bougie device of FIG. 1 showing a tip section, according to certain embodiments;

FIG. 4A is a schematic perspective view of the movable tip bougie device illustrating movement of the tip section between a tip angle of 60° and 90°, according to certain embodiments; and FIG. 4B is a schematic perspective view of the movable tip bougie device illustrating movement of the tip section between a tip angle of 30° and 50°, according to certain embodiments.

DETAILED DESCRIPTION

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed to a movable tip bougie device for facilitating introduction of an endotracheal tube into a trachea of a patient and for giving more control and manipulation during a tracheal intubation procedure. The movable tip bougie device includes a bougie section and a tip section movable relative to the bougie section based on an input from a practitioner during the tracheal intubation procedure. The tip section of the movable tip bougie device has a tip which is movable between 30° to 90° and allows an anesthesiologist to direct the tip anteriorly under the epiglottis and through the vocal cords, which may not be visible. The movable tip bougie device further includes a slide button which is connected to one end of a silk thread and another end of the silk thread is attached to the tip using a holder such that a linear movement of the slide button, by the practitioner, facilitates an angular movement of the tip during the tracheal intubation procedure.

Referring to FIG. 1, a schematic perspective view of a movable tip bougie device 100 is illustrated, according to an embodiment of the present disclosure. The movable tip bougie device 100 includes a bougie section 102 and a tip section 104 extending from the bougie section 102. The bougie section 102 and the tip section 104 together define an elongated body of the movable tip bougie device 100 which is generally inserted into a trachea of a patient and thereby helps as a guide to introduce an endotracheal tube during a tracheal intubation procedure. In an embodiment, the elongated body is substantially cylindrical or circular. In an example, a length of the elongated body of movable tip bougie device 100 is 70 cm. In an embodiment, the length of the elongated body of the movable tip bougie device 100 is from 30 cm to 110 cm, preferably from 40 cm to 100 cm, preferably from 50 cm to 90 cm, preferably from 60 cm to 80 cm, or 70 cm. The bougie section 102 includes a bougie body 108 an elongated hollow body, having a first end 108A and a first portion 108B that is continuous with the tip section 104. In some embodiments, the first end 108A of the bougie section 102 is substantially elliptical. In some embodiments, the first end 108A of the bougie section 102 may be spherical, cylindrical, or any other shape known in the art. The bougie section 102 further includes a silk thread 110 disposed within a body of the bougie body 108. The movable tip bougie device can include embodiments in which the connection made by the silk thread is a "retraction cord" 110. The silk thread 110 includes a first end 110A disposed within the bougie body 108 near the first end 108A thereof and runs through the body of the bougie 108 until the first portion 108B of the bougie body 108. A second end 110B of the silk thread 110 extends through an opening 112 defined in the first portion 108B of the bougie body 108 and attached to the tip section 104. In an embodiment, the silk thread 110 runs along first and second metal wires disposed in the interior of the bougie body 108 to guide the silk thread 110 through the elongated bougie body 108. In an embodiment, the first and second metal wires extend through longitudinal passageways that extend between the first end 110A to the opening 112 for the silk thread 110 to be threaded through. In an embodiment, a middle longitudinal passageway is spaced equidistantly between neighboring longitudinal passageways on either side of the middle longitudinal passageway. In an embodiment, the bougie body is substantially cylindrical and a ratio of the length of the bougie body to a width of the bougie body is from 5:1 to 20:1, preferably from 7.5:1 to 17.5:1, preferably from 10:1 to 15:1, or 12.5:1. In some embodiments, the silk thread 110 is a metal or a fiber. In an embodiment, the silk thread 110 runs through the bougie body 108 so that a longitudinal axis of the silk thread 110 is underneath and parallel to a longitudinal axis of the slide button 114, as seen in FIG. 1. The bougie section 102 further includes a slide button 114 located at the first end 108A of the bougie section 102. In an embodiment, the slide button is fabricated of plastic, ceramic, metal, a polymer, or a combination of the like. The slide button 114 is movably disposed in the body of the bougie body 108 in such a way that the slide button 114 is movable between a first position 'P1' and a second position 'P2' based on an input from a practitioner. The first position 'P1' of the slide button 114 may be defined as a position facing towards the tip section 104 and the second position 'P2' of the slide button 114 may be defined as a position opposite the first position 'P1' and facing towards the first end 108A of the bougie section 102. Moving the slide button 114 towards position P1 decreases an angle of the tip with respect to the bougie body 108 and moving the slide button towards position P2 increases an angle of the tip with respect to the bougie body 108. In an embodiment, the slide button 114 is attached to a hinge that moves with the slide button 114 when the slide button 114 is advanced toward the tip 116 (position P1) or retracted towards the bougie end 108A (position P2). In an embodiment, a length of the elongated body is from 1.5 to 3.5 times greater than a length between positions P1 and P2, preferably from 1.75 to 3.25 times greater, preferably from 2 to 3 times greater, preferably from 2.25 to 2.75 times greater, or 2.5 times greater. In an embodiment, the length between positions P1 and P2 is from 1.1 to 1.7 times greater than the width W of the elongated body, preferably from 1.2 to 1.6 times greater, preferably from 1.3 to 1.5 times greater, or 1.4 times greater. In an embodiment, the slide button 114 is movable not just linearly along the axis of the bougie body 108, but also circumferentially along the outer surface of the bougie body 108. In an embodiment, the slide button 114 is movable circumferentially along the outer surface of the bougie body 108. In essence, the practitioner using the device may have better control of the tip by moving the slide button 114 along a slit in the bougie body 108 that curves around a portion of the circumference of the bougie body. In an embodiment, the slit in the bougie body 108 has a depth that penetrates from 20% to 40% of the width W of the bougie body 108 preferably from 25% to 35%, or 30%. In an embodiment, the slit in the bougie body 108 is not linear but advances in "step stages" so that the practitioner has another means for tactilely determining the degree of extension or retraction of the tip. In essence, the "step stages" are grooves arranged in a non-linear fashion in the bougie body 108 as to aid the practitioner in adjusting the tip. In this aspect the slit extends along both the axis of the bougies body and along the circumference, e.g., up to about 30° along the circumference of the bougie body. In an embodiment, the slide button 114 is attached to the bougie body 108 by a screw, a hinge, or a clip, in a way that the practitioner can access the silk thread 110. Thus, the slide button 114 can be popped off and the silk thread retied in a quick and effective manner.

The tip section 104 further includes a tip 116 defined at a first end 104A thereof, a holder 118 disposed at the tip 116, and a recoiled wire 120 disposed within a body of the tip section 104. The tip section 104 has a second end 104B extending from the first portion 108B of the bougie body 108. In an embodiment, the length between P1 and P2 is from 1.1 to 1.5 times greater than a length between the first end 104A and second end 104B, preferably from 1.2 to 1.4 times greater, or 1.3 times greater. In an embodiment, the tip section 104 and the bougie section 102 may be an integral component of the movable tip bougie device 100. In some embodiments, the tip section 104 may be detachably attached to the bougie section 102. In some embodiments, the tip section 104 may be rigidly attached to the bougie section 102 to form a single body. The tip 116 of the tip section 104 is configured to bend at an angle 'α' of from 30° to 90° relative to the bougie body 108. The plane in which the bending occurs is the plane defined by the tip 116 and the silk thread 110. Similarly, the plane in which the bending occurs is also along the axis of the bougie body 108. In an embodiment, the tip section 104 is connected to the bougie section 102 through a hinge such as a tension hinge or polymer memory hinge and is configured to move towards the bougie section 102 on retraction of the slide button 114 and forward on pushing the slide button 114 forward or by natural tension of the hinge. The angle 'α' defined between a longitudinal axis of the bougie section 102 and a longitudinal axis of the tip section 104 is alternatively referred to as the tip angle 'α'. Particularly, the slide button 114 is configured to adjust the angle of the tip 116 relative to the bougie body 108 and the recoiled wire 120 is configured to prevent kinking of the tip 116 during the tracheal intubation procedure. In an embodiment, the recoiled wire 120 has a diameter of from 0.3 mm to 0.7 mm, preferably from 0.4 mm to 0.6 mm, or 0.5 mm. In some embodiments, the recoiled wire connects to attachment points positioned inside the tip 116, so that the attachment points are mounted where the recoiled wire zig-zags across the interior of the tip 116. Further, the attachment point is located where the recoiled wire is fixed horizontal between a first, rightmost end of the tip 116 and a second, leftmost end of the tip 116 as depicted in FIG. 1. The silk thread 110 extends through an outer surface of the tip 116 from the body of the bougie body 108 through the opening 112. In an embodiment, the opening has a guide to tightly fit the silk thread 110 from the body of the bougie body 108 to the outer surface of the tip 116. In an embodiment, the guide is positioned in the center of the opening 112. In an embodiment, the guide is substantially circular to guide the silk thread through it, and has a radius that is from 0.3 to 0.9 times the radius of the opening, preferably from 0.4 to 0.8, preferably from 0.5 to 0.7, or 0.6 times greater. The holder 118 located at the tip 116 of the tip section 104 is configured to hold the second end 110B of the silk thread 110 at the distal end 104A of the tip section 104. In an embodiment, the holder 118 is fabricated of polyvinyl chloride. In an embodiment, the holder 118 is a press-fit cap mounted on the tip 116 and is preferably fabricated of polyvinyl chloride. In an embodiment, the holder 118 is fabricated of a metal, an alloy, plastic, a ceramic, or a combination of the like.

As shown in FIG. 2, the slide button 114 is movably disposed at the first end 108A of the bougie section 102 and configured to slide into a groove 202 on an exterior surface of the bougie body 108 to adjust the angle of the tip 116. In some embodiments, the slide button 114 may have a rectangular shape or a square shape with rounded edges. In some embodiments, the slide button 114 may have an oval shape or an elliptical shape. In an embodiment, a minor axis of the elliptical slide button 114 is from 0.5 to 0.7 times greater than the width W of the bougie body 108, preferably 0.6 times greater. The slide button 114 includes a top surface 204 that helps the practitioner to firmly contact with a finger thereby to facilitate movement of the slide button 114 between the first position 'P1' and the second position 'P2'. In some embodiments, the top surface 204 may be defined as a matte surface, an embossed surface, or an engraved surface to allow firm contact with the finger of the practitioner. In some embodiments, the top surface 204 may include multiple protrusions or grooves in a specific pattern to help the practitioner to firmly touch the top surface 204 of the slide button 114. In some embodiments, the top surface 204 may include a coating to help the practitioner, wearing a glove, to firmly touch the top surface 204 with the glove still on, without the need to remove the glove during operation. The slide button 114 may further include a bottom surface (not shown) defined in conformance with a receiving portion 206 defined in the body of the bougie 108. The receiving portion 206 of the body of the bougie 108 may be configured to movably receive the slide button 114 therein and allow movement of the slide button 114 between the first position 'P1' and the second position 'P2'. The receiving portion 206 may have a length equal to or more than a distance defined between the first position 'P1' and the second position 'P2' of the slide button 114. The bottom surface of the slide button 114 may be aligned with the receiving portion 206 such that the slide button 114 may be slidably received within the receiving portion 206. The bottom surface of the slide button 114 is coupled with the first end 110A of the silk thread 110 disposed within the body of the bougie 108 such that the silk thread 110 is pulled when the slide button 114 moves to the first position 'P1'.

In some embodiments, the body of the bougie 108 includes at least seven grooves in which the slide button 114 slides into, and the slide button slides into an individual groove to adjust the angle of the tip 116 by at least 10°. In an embodiment, the seven grooves run perpendicular to an axis of the bougie body 108. In an embodiment, the body of the bougie 108 includes from 8 to 20 grooves, preferably from 10 to 18 grooves, preferably from 12 to 16 grooves, or 14 grooves. Each of the seven grooves may be defined in the receiving portion 206 of the body. The seven grooves may include a central groove, a first set of grooves defined adjacent the central groove facing towards the tip section 104, and a second set of grooves defined adjacent the central grooves opposite the first set of grooves and facing towards the first end 108A of the bougie section 102. The first set of grooves includes a first groove 202-1, a second groove 202-2, and a third groove 202-3 corresponding to a tip angle of 30°, 40°, and 50°, respectively, as such, each of the first groove 202-1, the second groove 202-2 and the third groove 202-3 helps to adjust the angle of the tip 116 by 10°. Particularly, the second groove 202-2 situated between the first groove 202-1 and the third groove 202-3 is equidistant from the first groove 202-1 and the third groove 202-3. Similarly, the second set of grooves includes a fifth groove 202-5, a sixth groove 202-6, and a seventh groove 202-7 corresponding to a tip angle of 70°, 80°, and 90°, respectively, as such, each of the fifth groove 202-5, the sixth groove 202-6 and the seventh groove 202-7 helps to adjust the angle of the tip 116 by 10°. The central groove may be alternatively referred to as the fourth groove 202-4 and corresponds to a tip angle of 60°. When sliding, the slide button 114 fits into the individual groove and is locked/clicked into place with the cam mechanism. The first groove 202-1, the second groove 202-2, and the third groove 202-3, the fourth groove 202-4, the fifth groove 202-5, the sixth groove 202-6, and the seventh groove 202-7 are collectively referred to as 'the grooves 202' and individually referred to as 'the groove 202' unless otherwise specifically mentioned. As such, the slide button 114 is actuated by the practitioner to move the tip 116 at the angle ranging from 30° to 90° relative to the bougie body 108. In an embodiment, when more than 7 grooves are employed, the slide button 114 helps adjust the angle of the tip 116 by less than 10°, preferably from 5° to 8° depending on the number of grooves selected.

The slide button 114 is movable between the first position 'P1' and the second position 'P2' along the body of the bougie 108, forming a slit between P1 and P2, such that a length of the slit the slide button 114 fits into is from 10% to 40% of an entire length of the bougie body 108, preferably from 15% to 35%, preferably from 20% to 30%, or 25%. In other words, the movement of the slide button 114 between the first position 'P1' and the second position 'P2' adjusts the angle of the tip 116 between 30° to 90°. Further, the slide button 114 has a degree of movement, in which it slides over a length of from 10% to 25% of the entire length of the bougie body 108, as seen in FIG. 1 preferably corresponding to the length of the slit. That is, the length between positions P1 and P2 has a length that is 10% to 25% that of the entire length of the bougie body 108. The first position 'P1' of the slide button 114 corresponds to the tip angle of 30° and the second position 'P2' of the slide button 114 corresponds to the tip angle of 90°.

In an embodiment, the slide button 114 has a top surface and a bottom surface and a flat circumferential edge between the top surface and bottom surface, wherein the flat circumferential edge includes a notch to engage with the bougie body 108. In some embodiments, the bottom surface of the slide button 114 may include a protrusion 208 configured to slidably engage with each groove 202. In an example, at the first position 'P1' of the slide button 114, the protrusion 208 may be engaged with the first groove 202-1 corresponding to the tip angle of 30° and the protrusion 208 may be engaged with the seventh groove 202-7 corresponding to the tip angle of 90°. In an embodiment, when clicked into place with the cam mechanism, the protrusion 208 is directly above and parallel to the individual groove it is clicked into.

As shown in FIG. 3, the movable tip bougie device 100 includes the tip section 104 having the second end 104B extending from the first portion 108B of the bougie body 108 and the first end 104A includes the tip 116. In some embodiments, the tip 116 includes one of a coude tip, a reverse coude tip, or a bullet tip. In some embodiments, the tip 116 is fabricated of polyvinyl chloride (PVC). In some embodiments, the tip 116 can be made of biodegradable and biocompatible rubber material such that the tip 116 can regain original position thereof after manipulation. For example, the shape of the tip may be varied as a blunt tip and/or a straight tip. A flexible region in the region may be provided to provide the tip 116 with agility and may be configured as a spring, or may be a flexible, unitary structure having a series of corrugations. When the flexible region is corrugated, it may be made from the same material as the tip 116. If desired, where a spring is utilized, it may be made from the same material as the tip 116, or may be formed from a non-metallic material, such as a medical grade plastic having sufficient resilience and stiffness qualities to function in a spring-like manner. Further, the tip section 104 may be made lighter than the bougie section 102 for easy maneuvering during the tracheal intubation process. The tip section 104 includes the recoiled wire 120 which is spirally wound around an interior of the tip 116. In an embodiment, the recoiled wire 120 is wrapped around a wire guide. In an embodiment, the recoiled wire 120 runs through hooks on each end of the interior of the tip 116 as to form a helical pattern. The recoiled wire 120 includes a first end 120A disposed proximal to the second end 104B of the tip section 104 and a second end 120B disposed proximal to the first end 104A of the tip section 104. Further, the recoiled wire 120 may have an outer diameter equal to an inner diameter of the tip section 104 such that the recoiled wire 120 may establish a firm contact with the interior of the tip section 104, and thereby kinking of the tip section 104 may be avoided. In some embodiments, the recoiled wire 120 zig-zags across the interior of the tip 116, so that the recoiled wire 120 runs from a first end of the interior of the tip 116, otherwise referred to as the second end 104B of the tip section 104, to a second end of the interior of the tip 116, otherwise referred to as the first end 104A of the tip section 104. The recoiled wire 120 also helps the tip section 104 to regain the original position thereof after manipulation. In an embodiment, the recoiled wire 120 is fabricated of stainless steel. In some embodiments, the recoiled wire 120 may be fabricated of a metal or a metal alloy which is biocompatible or biodegradable. The tip section 104 further includes a plurality of clippers 302 attached to an exterior surface thereof to align the silk thread 110 through the tip 116. In an embodiment, there are from 3 clippers to 10 clippers, preferably from 4 clippers to 9 clippers, preferably from 5 clippers to 8 clippers, or 6 clippers. Particularly, the second end 110B of the silk thread 110 that comes out of the body of the bougie 108 through the opening 112 defined at the first portion 108B thereof extends through the exterior surface of the tip section 104 and attached at the tip 116 of the tip section 104 using the holder 118. In some embodiments, the holder 118 may be an integral component of the tip section 104 and made of material identical to a material of the tip section 104. In some embodiments, the holder 118 may be an individual component detachably attached to the tip 116 of the tip section 104. In such a case, the holder 118 may be made of stainless steel identical to the recoiled wire 120. The plurality of clippers 302 helps to align the silk thread 110 on the exterior surface of the tip section 104. In some embodiments, the clippers 302 may be integral components of the tip section 104 and made of material identical to the material of the tip section 104. In some embodiments, the clippers

302 may be individual components detachably attached to the exterior surface of the tip section 104.

Referring to FIG. 4A, a linear movement of the slide button 114 towards the first end 108A of the bougie section 102 and corresponding angular movement of the tip section 104 between the tip angle 'α' from 60° to 90° relative to the bougie section 102 is illustrated, according to an embodiment of the present disclosure. In an example, the slide button 114 may be engaged with the fourth groove 202-4 of the body of the bougie 108 such that the tip 116 is angled at 60° with respect to the bougie body 108. When the slide button 114 is moved towards the first end 108A of the bougie section 102 at the second position 'P2', based on the inputs from the practitioner, the silk thread 110 attached between the slide button 114 and the tip 116 of the tip section 104 pulls the tip 116 towards the first end 108A such that the tip 116 is configured to bend from 60° to 90°. The fifth groove 202-5, the sixth groove 202-6, and the seventh groove 202-7 are defined in such a way that the slide button 114 is engaged with each groove 202 to controllably increase the angle 'α' of the tip 116 by 10°, from 60°, to 70°, to 80°, and finally to reach 90°. Further, by engaging the slide button 114 with the fifth groove 202-5, the sixth groove 202-6, and the seventh groove 202-7, the tip 116 is configured to bend at the angles 70°, 80°, and 90°, respectively.

Referring to FIG. 4B, a linear movement of the slide button 114 towards the first end 108A of the bougie section 102 and corresponding angular movement of the tip section 104 between the tip angle 'α' from 30° to 50° relative to the bougie section 102 is illustrated, according to an embodiment of the present disclosure. When the slide button 114 is moved towards the first end 108A of the bougie section 102 from the first position 'P1', the silk thread 110 attached between the slide button 114 and the tip 116 of the tip section 104 allows the tip 116 to bend from 30° to 50°. The first groove 202-1, the second groove 202-2, and the third groove 202-3 are defined in such a way that the slide button 114 is engaged with each groove 202 to controllably increase the angle 'α' of the tip 116 by 10° to reach 50°. Further, by engaging the slide button 114 with the first groove 202-1, the second groove 202-2, and the third groove 202-3, the tip 116 is configured to bend at the angles 30°, 40°, and 50°, respectively. After the manipulation, the slide button 114 may be moved towards the distal end 104A of the tip section 104 from the second position 'P2' to the first position 'P1' such that the tip 116 may move by 10° to travel from 90° to 30° due to elastic properties of the materials of the tip section 104. As such, the slide button 114 may be moved towards the first end 108A of the bougie section 102 and the distal end 104A of the tip section 104 to move the tip 116 of the movable tip bougie device 100 between 30° and 90° to easily maneuver during the tracheal intubation procedure.

Numerous modifications and variations of the present disclosure are possible in light of the above teachings. It is therefore to be understood that within the scope of the appended claims, the invention may be practiced otherwise than as specifically described herein.

The invention claimed is:

1. A movable tip bougie device, comprising:
   a tip section and a bougie section;
   wherein the bougie section comprises a bougie body, a silk thread, and a slide button located at a first end of the bougie section;
   wherein the slide button is configured to mechanically adjust an angle of a tip disposed on a distal end of the tip section relative to the bougie body by action of the slide button through the silk thread; and
   wherein a first end of the silk thread is connected to the slide button and a second end of the silk thread is connected to the tip;
   the tip section includes the tip, a holder, and a recoiled wire;
   wherein the silk thread extends through an outer surface of the tip and through an opening of the bougie body; and
   the holder is configured to hold the silk thread at the distal end of the tip section; and
   the recoiled wire is helically coiled around the tip; and
   the tip section is connected to the bougie section through a hinge and is configured to move backwards toward the bougie section on retraction of the slide button and forward on pushing the slide button forward.

2. The device of claim 1, wherein the tip is fabricated of polyvinyl chloride (PVC).

3. The device of claim 1, wherein the slide button has a top surface and a bottom surface and a flat circumferential edge between the top surface and bottom surface, wherein the flat circumferential edge includes a notch to engage with the bougie body.

4. The device of claim 3, wherein the body of the bougie has at least seven grooves in which the slide button slides into an individual groove to adjust the angle of the tip by at least 10°.

5. The device of claim 1, wherein the recoiled wire is fabricated of stainless steel.

6. The device of claim 1, wherein the recoiled wire is spirally wound around an interior of the tip.

7. The device of claim 1, wherein the tip section further includes a clipper to align the silk thread through the tip.

8. The device of claim 1, wherein the silk thread is a fiber.

9. The device of claim 1, wherein a length of a slit is from 5% to 40% of an entire length of the bougie body.

10. The device of claim 1, wherein the tip is configured to bend from 60° to 90° relative to a longitudinal axis of the bougie body when the slide button slides towards the first end of the bougie section.

11. The device of claim 1, wherein the tip is configured to bend from 30° to 50° relative to a longitudinal axis of the bougie body when the slide button slides towards the first end of the bougie section.

12. The device of claim 1, wherein the bougie body is substantially cylindrical and a ratio of a length of the bougie body to a width of the bougie body is from 5:1 to 20:1.

13. The device of claim 1, wherein the recoiled wire is helically coiled against an interior surface of the tip, so that the recoiled wire runs from a first end of the interior of the tip to a second end of the interior of the tip.

14. The device of claim 1, wherein the first end of the bougie body is substantially elliptical.

15. The device of claim 1, wherein the silk thread runs through the bougie body so that a longitudinal axis of the silk thread is underneath and parallel to a longitudinal axis of the slide button.

16. The device of claim 1, wherein the tip includes one of a coude tip, a reverse coude tip, or a bullet tip.

17. The device of claim 4, wherein a second groove situated between a first groove and a third groove is equidistant from both the first groove and the third groove.

* * * * *